United States Patent [19]

Bernstein et al.

[11] Patent Number: 5,478,750

[45] Date of Patent: Dec. 26, 1995

[54] METHODS FOR PHOTOMETRIC ANALYSIS

[75] Inventors: Daniel M. Bernstein, San Mateo; Paul J. Lingane, Palo Alto; Robert Nagle, Mountain View; Vladimir E. Ostoich, Los Altos, all of Calif.

[73] Assignee: Abaxis, Inc., Sunnyvale, Calif.

[21] Appl. No.: 292,558

[22] Filed: Aug. 18, 1994

Related U.S. Application Data

[63] Continuation of Ser. No. 40,549, Mar. 31, 1993, abandoned.

[51] Int. Cl.⁶ .................................................. G01N 21/17
[52] U.S. Cl. ............................ 436/164; 436/8; 436/165; 422/55; 422/64; 422/65; 422/67; 422/101
[58] Field of Search .................................. 422/55, 64, 65, 422/67, 101; 436/8, 164, 165

[56] References Cited

U.S. PATENT DOCUMENTS

| Re. 31,149 | 2/1983 | Ginsberg et al. | 422/64 |
|---|---|---|---|
| 3,833,864 | 9/1974 | Kiess et al. | 356/184 |
| 3,941,487 | 3/1976 | Ehret et al. | 356/181 |
| 4,059,357 | 11/1977 | Klein | 356/243 |
| 4,176,958 | 12/1979 | Way et al. | 356/321 |
| 4,195,932 | 4/1980 | Popelka | 356/407 |
| 4,437,762 | 3/1984 | Glenn et al. | 356/326 |
| 4,437,763 | 3/1984 | Kaye | 356/326 |
| 4,446,871 | 5/1984 | Imura | 128/633 |
| 4,536,369 | 8/1985 | Sakurada et al. | 422/65 |
| 4,566,110 | 1/1986 | Kolber | 422/91 X |
| 4,629,703 | 12/1986 | Uffenheimer | 436/45 |
| 4,687,329 | 8/1987 | Schultz | 356/328 |
| 4,694,833 | 9/1987 | Hamaguri | 128/633 |
| 4,744,657 | 5/1988 | Aralis et al. | 356/391 |
| 4,773,422 | 9/1988 | Isaacson et al. | 128/633 |
| 4,785,407 | 11/1988 | Sakagami | 364/497 |
| 4,826,319 | 5/1989 | Namba et al. | 356/339 |
| 5,061,381 | 10/1991 | Burd | 210/789 |
| 5,122,284 | 6/1992 | Braynim et al. | 210/782 |
| 5,183,638 | 2/1993 | Wakatake | 422/64 |
| 5,204,264 | 4/1993 | Kaminer | 436/8 |
| 5,204,264 | 4/1993 | Kaminer | 436/8 |
| 5,212,094 | 5/1993 | Ogawa | 436/47 |
| 5,219,526 | 6/1993 | Long | 422/64 |
| 5,230,863 | 7/1993 | Salpeter | 422/67 |
| 5,234,835 | 8/1993 | Nestor et al. | 436/11 |
| 5,242,803 | 9/1993 | Burtis et al. | 435/7.92 |

FOREIGN PATENT DOCUMENTS

| 0167750 | 1/1986 | European Pat. Off. . |
| 2150704 | 7/1985 | United Kingdom . |

*Primary Examiner*—James C. Housel
*Assistant Examiner*—Harold Y. Pyon
*Attorney, Agent, or Firm*—Townsend and Townsend and Crew

[57] ABSTRACT

The present invention provides a compact, highly automated photometric analyzer for measuring the concentration of substances found in a fluid, typically a blood sample or other body fluid sample taken from a patient. The operator places a small quantity of the sample into a special rotor and then loads the rotor into the analyzer. The analyzer accepts the rotor, centrifuges and dilutes the sample, and distributes the sample into a plurality of cuvettes near the outer edge of the rotor. Some of these cuvettes hold reagents which react with the sample. The analyzer then measures light absorption within the sample at a number of preselected frequencies. According to the present invention, a pair of specially designed apertures direct light from the sample through a plurality of beam splitters, interference filters, and associated photodetectors. The system also includes means for performing automatic calibration and error checking functions. These means include a through hole through the rotor, and an opaque body carried by the rotor. Additionally, measurements may be repeated through a given cuvette and the results averaged to minimize the effect of random variations between measurements.

3 Claims, 5 Drawing Sheets

METHODS FOR PHOTOMETRIC ANALYSIS

This is a Continuation of application Ser. No. 08/040,549 filed Mar. 31, 1993, now abandoned.

BACKGROUND OF THE INVENTION

1. Field of the Invention

The present invention relates generally to the determination of fluid chemistries by photometric analysis. More particularly, the present invention provides a simple, compact, and reliable photometric system in which a fluid sample, which is typically blood or another body fluid, e.g., urine, saliva, serum, or plasma, is automatically separated and analyzed to simultaneously measure the concentration of a number of fluid components.

2. Description of the Background Art

Methods for the photometric determination of fluid chemistry are known in the art. According to such methods, a sample is drawn from the patient and then, in the case of blood, typically centrifuged to separate the blood plasma from the blood's cellular components. After centrifugation, quantities of the separated fluid are mixed with one or more reagents. The various fluid-reagent mixes are then placed into sample cuvettes and light of predetermined wavelengths is passed through the cuvettes. This light is partially absorbed by the products of the reactions between the reagents and components of the fluid. The degree to which the light is absorbed is dependant upon the concentration of the reaction product in the fluid sample.

By comparing the intensity of the light transmitted through the cuvette with a reference intensity, the concentration of a given product of the reaction between the fluid and the reagent can be determined. The concentration of the reaction product is then used to calculate the concentration of a corresponding component in the sample fluid.

Apparatus for performing photometric analysis of fluids including blood samples is known in the art. However, known systems are in general cumbersome and expensive. Moreover, use of these known systems is labor intensive, time-consuming, and generally requires highly skilled laboratory personnel.

It would therefore be desirable to provide a compact, relatively inexpensive, and highly automated system for the rapid centrifugation, analysis, and measurement of components present in fluids including blood or other body fluid samples. It would be desirable if such a system were sufficiently inexpensive to be purchased by hospitals and small clinics so that fluid analysis could be performed on site rather than at a special laboratory located elsewhere. It would further be desirable if such a system were sufficiently automated so that it could be used reliably and with great precision even by a person with little or no specialized training.

SUMMARY OF THE INVENTION

The present invention provides apparatus and methods for photometric analysis for determining the concentration of a substance carried by a blood sample or other fluid sample held in a rotor having a number of sample cuvettes. According to one aspect of the invention, light from a light source, which may be an arc lamp, is directed through a reacted sample, a pair of apertures, and onto a light detector. The apertures are sized and positioned so that all light directed onto the detector has traversed one of the cuvettes and so that light from the full width of the light source is directed onto the detector.

According to another aspect of the invention, the analyzer system has a number of beam splitters through which light from the apertures is directed to reflect portions of the light onto light detectors.

The invention also provides methods for calibrating the light detectors and for minimizing potential measurement errors. One of these methods utilizes an opaque body carried by the rotor to prevent light from passing through the rotor. Another uses a through hole to allow light to pass freely through the rotor to allow calibration of the detectors. Another method involves making and averaging multiple measurements through a single cuvette in order to minimize the effects of random errors during any single measurement.

DESCRIPTION OF SPECIFIC EMBODIMENTS

The present invention provides a compact, highly automated photometric analyzer system for determining the concentration of various components present in a fluid sample, which may be a blood sample or other body fluid sample taken from a patient.

Figure 1:
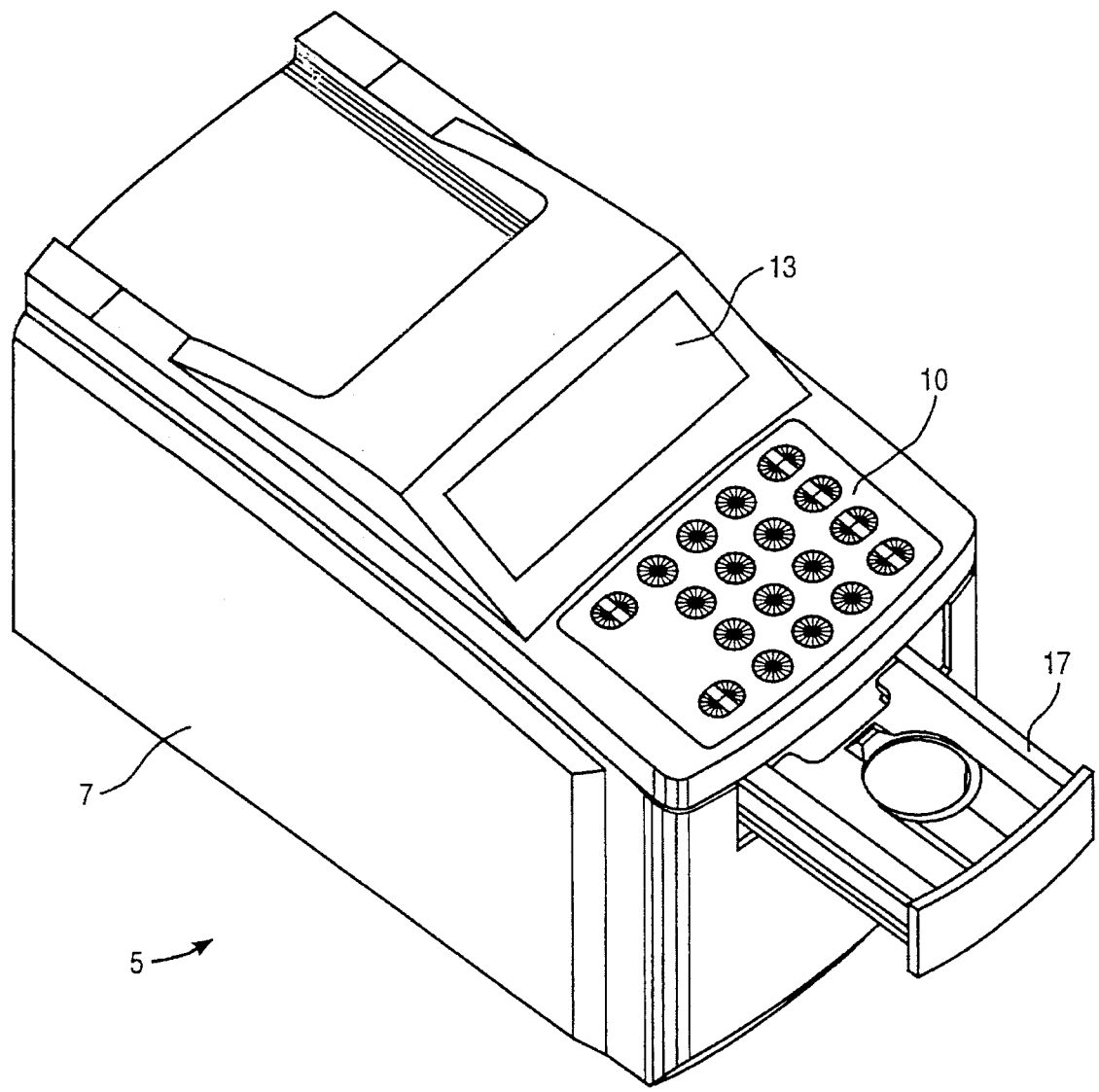
FIG. 1 is an perspective drawing showing the exterior of a photometric fluid analyzer according to the present invention.

FIG. 1 depicts an analyzer according to the present invention. As depicted in FIG. 1, analyzer 5 comprises an exterior housing 7, an input keyboard 10, a liquid crystal display 13, and a motorized sliding tray 17. Sliding tray 17 is adapted to receive a special sample rotor. The rotor is described in more detail below.

Figure 2:
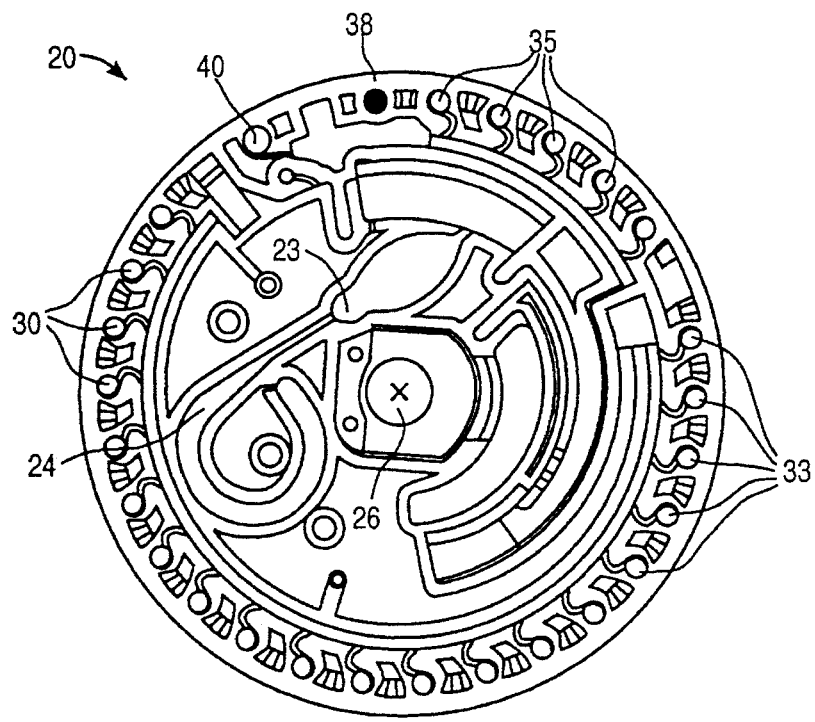
FIG. 2 is a plan view of a sample rotor for use with the analyzer.

FIG. 2 is a plan view of a sample rotor suitable for use in an analyzer according to the invention. Sample rotor 20 is in the form of a circular disk suitable for loading into the sliding tray of the analyzer unit. The rotor is made of molded plastic and is approximately 8 cm in diameter by 2 cm thick. The configuration of the rotor is not a primary aspect of the present invention. Further details of the rotor construction may be found in U.S. Pat. Nos. 5,061,381; 5,173,193; 5,186,844; 5,122,284; and U.S. patent application Ser. Nos. 07/747,179; 07/783,041; 07/833,689; and 07/862,041, the complete disclosures of which are incorporated herein by reference. For the purpose of understanding the present invention, it is sufficient to note that the rotor comprises a series of many interlinked internal chambers and passages and that movement of fluid through the rotor is controlled by a series of stop junctions, capillaries, and siphons acting in conjunction with centrifugal force applied by spinning the rotor.

Sample rotor 20 is designed for the analysis of a blood sample taken from a patient. The rotor has a blood application site 23, a blood overflow container 24, a diluent container 26, and a plurality of cuvettes 30, including assay cuvettes 33 and reference cuvettes 35, disposed along the outer edge of the disk. The rotor is used as follows. First, a blood sample is taken from a patient. The blood sample may be taken from a vein or from a finger stick. The sample need not be precisely measured; between 40 and 100 microliters of blood is sufficient. The operator of the system applies the sample to blood application site 23. The rotor is then placed into sliding tray 17 (FIG. 1) of the analyzer. The tray accepts the rotor and retracts into the body of the analyzer in a manner similar to the sliding tray on a compact disk player. When the tray closes, a spindle coupled to a motor engages the bottom of the sample rotor. The spindle causes diluent container 26 to open, thereby allowing the diluent to mix with a predetermined amount of the blood sample. Excess blood from the sample flows into blood overflow container 24 and is held there inside the rotor.

As the rotor spins inside the analyzer, the blood sample mixes to homogeneity with the diluent. As the rotor continues to spin, the blood cells are separated from the diluted plasma by centrifugal force. Other rotors could be designed in which separation of the blood cells occurs before dilution of the plasma. After separation and mixing, the diluted plasma is distributed through the internal channels of the rotor into cuvettes 30.

Some of the cuvettes are assay cuvettes 33. These assay cuvettes hold specially formulated reagent beads. The reagent beads dissolve in the plasma and chemical reactions are initiated between components of the diluted plasma and the reagent beads. Other cuvettes serve as reference cuvettes 35. Chemical reactions with the fluid sample do not take place in the reference cuvettes. Instead, the contents of the reference cuvettes are compared with the contents of the assay cuvettes as part of the test procedure.

The chemical reactions taking place in the assay cuvettes are monitored photometrically. Up to fifty different tests can be performed automatically by the analyzer. Some of the tests are endpoint tests, that is, the result is computed based on the amount of a given reaction product left in the cuvette when the reaction is completed. For endpoint tests, the analyzer makes a series of measurements and compares them with one another until criteria are met that indicate the reaction has gone to completion.

Other tests are rate tests, which depend on the rate of formation of a known reaction product within the cuvette. Each test is performed by the analyzer according to known and accepted analytical procedures. For rate tests, the analyzer compares successive measurements and computes the rate at which the reaction product is being formed.

One of the cuvettes holds an opaque body 38, which may be in the form of a black ball or disk. Opaque body 38 completely blocks light transmission through the cuvette. The opaque body serves as a reference cuvette for the elimination of offsets in the system electronics. This compensation procedure is described further below.

Finally, one of the cuvettes is in the form of a through hole 40, a physical opening through the body of the rotor. The through hole may serve as a reference cuvette for comparison with one of the assay cuvettes in which a known reaction takes place. Through hole 40 also makes possible a special "full scale" calibration of the system electronics. Both of these functions are described below.

The analyzer system has a highly compact optical system, which allows for the simultaneous measurements of light absorption at a plurality of wavelengths. The optical system is depicted schematically in FIG. 3. As depicted therein, white light (comprising a continuum of wavelengths) from an arc lamp 45 is reflected by a mirror 47 through one of the cuvettes 30 of rotor 20.

Use of an arc lamp is highly advantageous, especially in an analyzer of this size. A high intensity light source provides a high signal to noise ratio. The arc lamp used in the present embodiment discharges approximately 0.1 joules of energy during a flash of approximately 5 microseconds ($5 \times 10^{-6}$ seconds) duration. Thus, during the brief time that the arc lamp is illuminated, it discharges energy at a rate of some 20,000 watts. Because the arc lamp flash is so brief, the average power consumption is far less than would be the case with a continuous source of light such as an incandescent lamp. Use of an incandescent lamp operating (and therefore producing heat) at an average power consumption of 20,000 watts would be highly impractical.

The arc lamp also produces its high intensity light in a very small gap. The electric arc found in the present embodiment is only about 1.5 millimeters in width. In an electric arc lamp, the arc width corresponds closely to the distance between the electrodes. This very small light source facilitates the compact design of the rest of the optical system and in particular, the use of compact sample cuvettes having diameters and optical path lengths of just a few millimeters. Rotors presently in use have cuvettes with lengths of 1.7, 2.1, 4.3, and 5.0 mm, and diameters of about 4 mm or less.

Referring again to FIG. 3, light from arc lamp 45 is partially absorbed by the contents of cuvette 30. The degree to which the light is absorbed is dependant upon the light wavelength and upon the contents of the cuvette, i.e., what chemical constituents are present and in what concentrations. After exiting the cuvette, the light travels through apertures 50 and 52 and through a collimating lens 54.

Figure 3:
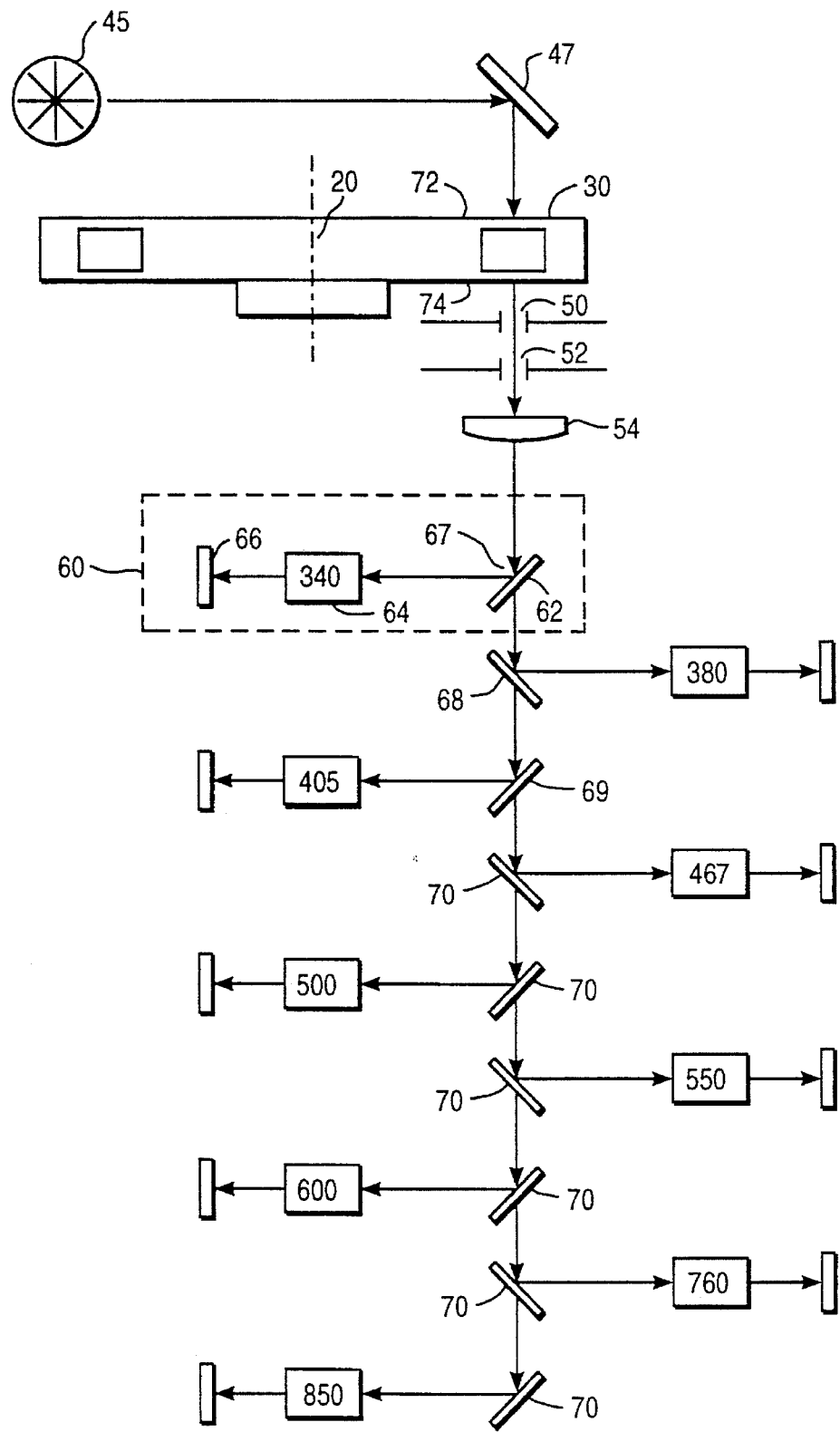
FIG. 3 is a schematic diagram depicting the optical path taken by light through the analyzer.

After exiting lens 54, the collimated light passes through a series of detector assemblies 60. Each detector assembly 60 comprises a beam splitter 62, an interference filter 64, and a photodetector 66. In the present embodiment, the first three beam splitters 67, 68, and 69 are wavelength discriminating. First beam splitter 67 reflects light having a wavelength less than approximately 360 nanometers and transmits light having a wavelength above that. Similarly, second and third beam splitters 68 and 69 reflect light having wavelengths below 395 and 415 nanometers, respectively. It has been found that use of these three wavelength discriminating beam splitters results in sufficient light being transmitted to allow for a series of nine beam splitters and associated detector assemblies as depicted in FIG. 3. At present, beam splitters 70 are in the form of simple unsilvered glass plates. Each of these glass plates reflects about six percent of all light falling upon it (substantially irrespective of wavelength).

Associated with each beam splitter are an interference filter 64 and a photodetector 66. The interference filters filter out all light except that having a wavelength within a narrow band centered about a preselected value. The wavelengths passed by the interference filters are, from the first detector assembly to the last, as follows: 340, 380, 405, 467, 500, 550, 600, 760 and 850 nanometers. These wavelengths were chosen to correspond to the chemical reactions taking place between the dilute samples and the reagent beads in the rotor. As a result, each of the photodetectors detects substantially monochromatic light having a wavelength preselected to match the clinical chemistries used in the various assay cuvettes of the rotor. This system of serial detector assemblies allows for the measurement of light absorption at a number of discrete wavelengths simultaneously within a single cuvette.

As can be seen in FIG. 3, the individual detector assemblies 60 are disposed in a "zig-zag" pattern in which the photodetectors are arrayed in an alternating pattern on opposite sides of the light path. This is advantageous because the light path is offset somewhat as the light is transmitted through the beam splitters. This alternating pattern means that the offset in a given beam splitter is corrected by a corresponding (opposite) offset in the next beam splitter. This correction helps to ensure that every photodetector is exposed to an equivalent view of the lamp and the cuvette.

One of the wavelengths for which light absorption is measured is 850 nanometers. This particular wavelength is unaffected, i.e., not absorbed, by the products of the chemical reactions relied upon in the testing procedures. Any light absorbed at 850 nanometers must therefore be due to phenomena other than the analytical reactions taking place in the cuvettes. The 850 nanometer light is affected by these other extraneous phenomena to almost exactly the same degree as light having the selected measurement wavelengths. Thus, intensity of the light at 850 nanometers is available for use as a convenient reference intensity.

This is done as follows. First, measurements are taken and recorded at 850 nanometers and simultaneously through the same cuvette (using the same lamp flash) at one or more selected wavelengths responsive to a chemical reaction taking place in the test cuvette. Simultaneous measurement at a number of wavelengths is advantageous in that the detectors are thereby exposed to the same image taken during the same lamp flash and errors due to differences between individual flashes or variations in cuvette position are thereby minimized.

Next, measurements are taken at 850 nanometers and simultaneously at the same analytical wavelengths through a reference cuvette. The reference cuvette may be the through hole in the rotor, or a cuvette in which the chemical reaction of interest is not taking place because the active reagent is not present. By comparing the light detected at the wavelength of interest and at 850 nanometers through both the assay cuvette and the reference cuvette, differences between the measurements due to differences between the two cuvettes are eliminated from the calculations of the concentrations of the various reaction products. These differences may arise from e.g., surface scratches on one of the cuvettes, suspended particulate matter in one of the cuvettes, or from variations in the intensity of the light between flashes of the lamp. Although a process has been described in which measurements are taken through a test cuvette prior to measurements through a reference cuvette, the actual order of these steps is not significant.

Figure 4:
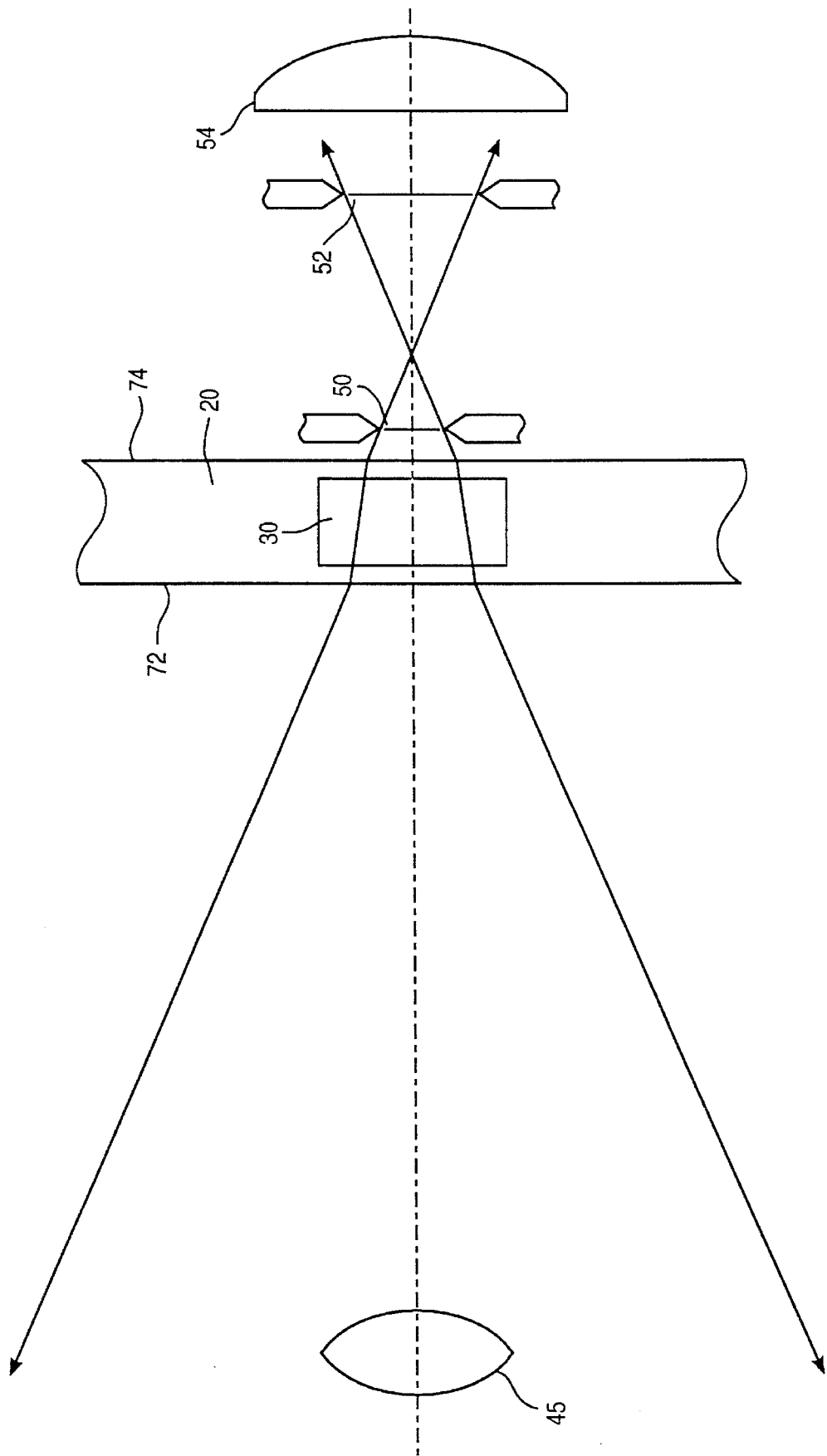
FIG. 4 is an illustration showing the interrelationship of an arc lamp, a sample cuvette, and a pair of apertures within the analyzer.

The relative positions of arc lamp 45, rotor 20 including a cuvette 30, and apertures 50 and 52 are depicted in FIG. 4. FIG. 3 shows a mirror 47 disposed between arc lamp 45 and rotor 20. Mirror 47, however, merely changes the direction of the light path between the lamp and the rotor by 90°. For clarity, the mirror has therefore been omitted from FIG. 4.

As FIG. 4 illustrates, apertures 50 and 52 are positioned and sized to meet two independent criteria. First, the apertures limit light entering the region of the detectors to light which has traversed cuvette 30. This is beneficial in that the detectors are allowed to "see" only the cuvette and the effects of extraneous conditions are thereby minimized.

Second, the positions and sizes of apertures 50 and 52 relative to arc lamp 45 are such that light from across the full width of the lamp is allowed to enter the detectors. In an arc lamp such as that used in the present embodiment, the position of the arc between the electrodes may vary somewhat between from flash to flash. Both the intensity and the spectral content at a given position between the electrodes may therefore vary significantly from one flash to another. However, the total energy discharged across the arc and the average spectral content of the full arc will be very nearly constant from flash to flash. Sizing the apertures to allow light from across the full width of the arc to strike the detectors minimizes the effect of variations between individual flashes.

The dimensions used in the present embodiment are as follows. The optical path length between the center of arc lamp 45 and the top 72 of rotor 20 is approximately 50 mm. In the analyzer, this path length is equal to the sum of the distance between the center of lamp 45 and mirror 47 (FIG. 3) and the distance between the mirror and the top 72 of rotor 20. The distance between the top 72 and bottom 74 of rotor 20 is about 8 mm. The optical path length through cuvette 30 varies depending on the clinical chemistry employed. Cuvettes having lengths of 1.7, 2.1, 4.3, and 5.0 mm are used for different analytical reactions.

First aperture 50 is a circular (pinhole) aperture having a diameter of 0.5 mm. First aperture 50 is positioned about 2 mm from the bottom 74 of rotor 20. Second aperture 52 is a circular aperture 1.0 mm in diameter. Second aperture 52 is positioned 15 mm away from first aperture 50. Finally, collimating lens 54 is located with its flat surface 2.5 mm away from second aperture 52. Lens 54 has a focal length of 15 mm. Once the light has left collimating lens 54 the exact positions of the individual beam splitters are not critical so long as they are positioned further along the light path.

The above dimensions were derived empirically and by graphical analysis to satisfy the two criteria mentioned above: 1) the photodetectors are allowed to see only light that has traversed the cuvette; and 2) the photodetectors are exposed to light from the full width of the lamp. Additionally, a ray tracing software program was used as an aid in sizing and positioning collimating lens 54. Lens 54 was designed to minimize the cross sectional area of the illuminating beam so that the size of the detectors could likewise be minimized consistent with each detector being exposed to light from the full width of the lamp. These considerations contribute to the exceedingly compact construction of the entire system. Notably, the distance between first aperture 50 and the last of the nine beam splitters is only about 65 mm.

Figure 5:
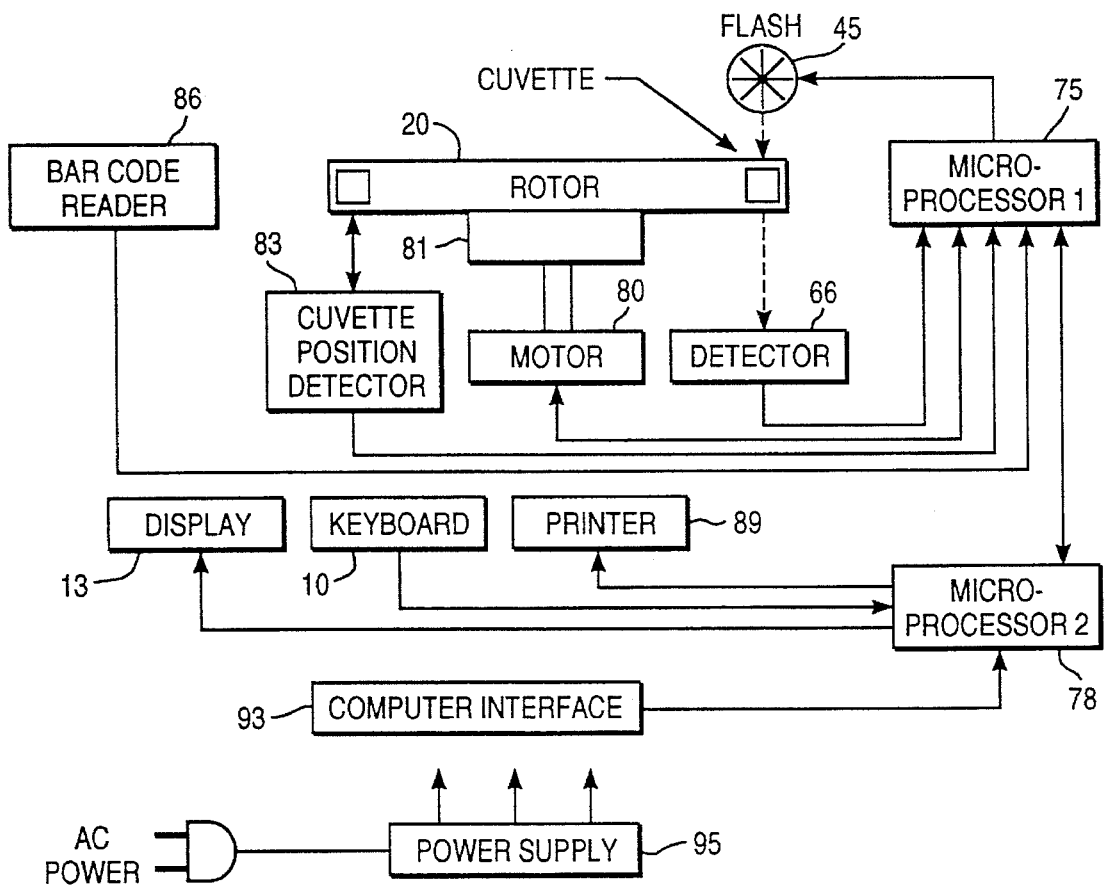
FIG. 5 is a schematic diagram depicting control of various analyzer system functions by a pair of microprocessors.

The system functions are controlled by two microprocessors as depicted in FIG. 5. In the present embodiment, first and second microprocessors 75 and 78 are Intel 80C196 microprocessors. First microprocessor 75 controls the measurement functions while second microprocessor 78 specializes in user-interface functions.

First microprocessor 75 controls the speed and acceleration of motor 80, which is coupled to a spindle 81 for engagement with rotor 20; monitors a cuvette position detector 83; controls the measurement electronics; and processes data from the photodetectors 66. First microprocessor 75 also interfaces with a bar code reader 86, which reads a bar code printed around the perimeter of the rotor. The bar code identifies the type of rotor and carries calibration information specific to the chemical lots of the reagents used in that rotor.

First microprocessor 75 controls the flashing of arc lamp 45 based on information from cuvette position detector 83. The sample rotor has a pattern of mirrored elements around its rim whose positions are monitored with great precision by cuvette position detector 83. The microprocessor ensures that the lamp is flashed at a time when one of the cuvettes is properly aligned with the apertures.

The timing of the flashes is therefore dependant upon the speed of the rotor. In the present embodiment, the rotor spins during measurement at approximately 1200 rpm and the lamp flashes through one cuvette per rotor revolution. The time between lamp flashes is therefore about 50 milliseconds. At this *** single cuvette traverses the apertures in about 100 microseconds.

Second microprocessor 78 completes the calculation of analytical results from data that were transferred from the first microprocessor. Additionally, the second microprocessor controls keyboard 10, through which the user can input information such as an operator number or a patient identification number. This microprocessor also controls liquid crystal display 13 and a printer 89. The printer prints the test results for convenient reference by a physician or other caregiver. Finally, second microprocessor 78 is connected to an RS-232 computer interface 93, through which the analyzer may be connected to a host computer for the convenient uploading of information for record keeping and billing, as well as for tracking quality-control parameters. Information may also be input to the analyzer from a computer through interface 93. The entire system is powered by standard household power through a power supply 95. Alternatively, portable analyzer systems can utilize battery power.

Figure 6:
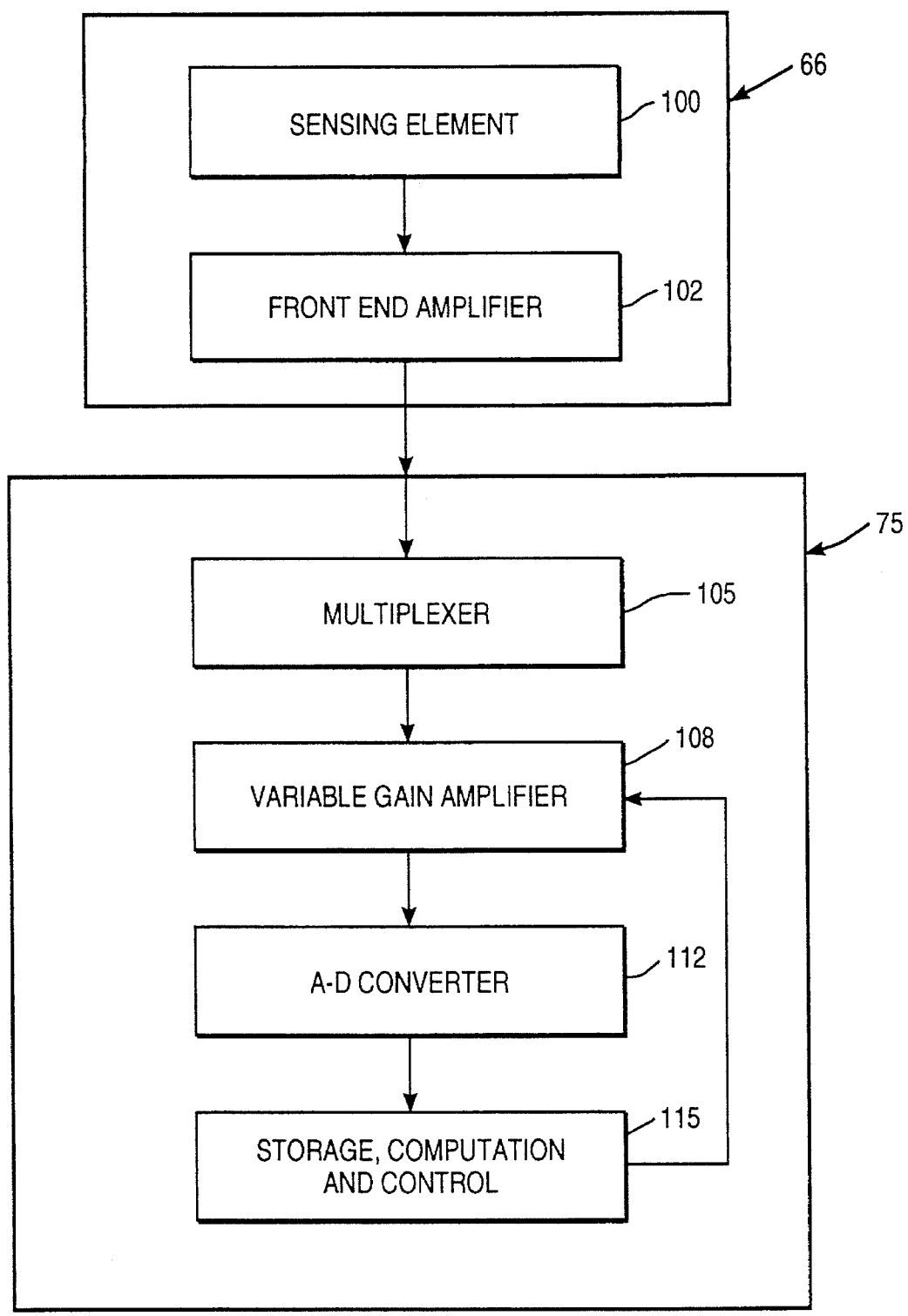
FIG. 6 is a schematic diagram depicting the processing of signals from a light detector by elements of one of the microprocessors.

Processing of signals from the photodetectors 66 is depicted schematically in FIG. 6. As indicated therein, each of the nine photodetectors 66 comprises a sensing element 100 and a front end amplifier 102. Light energy impinging on sensing element 100 is converted into an amplified electrical signal by front end amplifier 102 before being sent to first microprocessor 75. The first microprocessor, whose function is described above, includes circuitry that functions as a multiplexer 105, a variable gain amplifier 108, an analog-to-digital converter 112, and storage, computation, and control means 115.

As noted, there are actually nine detectors (one for each beam splitter) coupled to the microprocessor. For clarity, only one of these detectors is depicted in FIGS. 5 and 6. Multiplexer 105 of microprocessor 75 selectively couples the microprocessor to the detectors so that signals are received from one selected detector at a time. Multiplexer 105 includes sample and hold means in which a signal level is temporarily stored for later processing. From the multiplexer, the signal is sent to a variable gain amplifier 108, which allows for calibration of the signal as is described further below. The analog signal level is then converted to a digital value in analog-to-digital converter 112 before being sent to storage, computation, and control circuitry 115.

Calibration levels are calculated by microprocessor 75 so that variable gain amplifier 108 can be adjusted to provide a near optimum full scale signal to analog-to-digital converter 112. As is described above, sample rotor 20 has a through hole 40 near its outer edge in the place of one of the cuvettes. Prior to the computation of chemical concentrations, light is flashed through the through hole 40 onto the detectors. For each detector, variable gain amplifier 108 is adjusted until the signal output from that detector 66 to analog-to-digital converter 112 is near the maximum input level of the converter. In the current embodiment, variable gain amplifier 108 is adjusted to output a signal equal to ninety percent of the converter's maximum input level.

The computed full-scale gain level for the variable gain amplifier is determined and stored in first microprocessor 75 separately for each detector. When measurements are being taken later, the stored gain levels are applied to the detector signals by variable gain amplifier 108 under the control of first microprocessor 75. This calibration procedure allows the detectors to take advantage of nearly the full range of the analog-to-digital converter without exceeding its range.

The calibration procedure also compensates automatically for the decreasing brightness of the lamp as it ages. As the light from the lamp grows progressively more dim, the optimal gain levels calculated and stored for each detector will increase to a corresponding degree. This insures that nearly the full range of the analog-to-digital converter will be utilized throughout the life of the lamp.

Aging of the lamp is monitored automatically by the system. Each time a new rotor is loaded, a value corresponding to the measured intensity of the lamp through the through hole is compared to a value stored in the microprocessor. The stored value corresponds to the intensity of the lamp when new. When the measured intensity drops to a preselected fraction, typically about 50 percent, of the original intensity, an indicator signal is sent to the LCD display to indicate to the operator of the system that the lamp should be changed.

A related procedure is provided for detecting errors which might occur due to contamination of the optical system or other problems in the analyzer. Historical information, typically a running average, corresponding to the lamp intensity as measured through the through hole is stored and maintained in the microprocessor. Should any one measurement diverge too widely from the running average, an error indication is displayed. In case of contamination of the optics, problems with the power supply, or other problems with the system, the indicated intensity of the lamp would suddenly decrease. This sudden divergence from the running average would trigger the error indication.

Another procedure is provided for compensating for erroneous signals in the apparatus electronics. Even when no light impinges on the detectors, a small signal may still be measured from them. This current, which can be referred to as "dark current" since it is found with no light impinging the photodetectors, is a possible source of error in the light measurements. Accordingly, means are provided to subtract this "dark current" from the light levels measured by the detectors.

As described above in connection with FIG. 2, sample rotor 20 has an opaque body 38 in the place of one of the cuvettes. Although this opaque body is a solid object in the present embodiment, it could be in the form of a cuvette filled with a liquid dyed sufficiently dark to be effectively opaque.

In the present embodiment, the lamp is flashed and the detectors read while opaque body 38 is aligned with the apertures to prevent light from the lamp from impinging on the detectors. Any signals in the detectors will therefore be erroneous, due either to false current offsets within the system electronics or to stray light striking the detectors. For each detector, a corresponding "dark current" value is stored in the microprocessor for later subtraction from the values measured by the detectors during the measurement process.

During the measurement process, light intensity measurements are taken through both sample cuvettes (in which the reaction of interest takes place) and reference cuvettes (in which the reaction does not take place). The measurements are then compared with one another to determine the degree of light absorption due to a known reaction product.

According to one aspect of the present invention, multiple measurements are taken through a single cuvette and averaged to eliminate errors due to random noise. As the rotor spins, a given cuvette passes the apertures once during each revolution of the rotor. Each time the cuvette passes by the apertures, the arc lamp is flashed, and measurements are taken and stored for later calculations. By storing and averaging measurements from multiple flashes through a given cuvette, the effect of random variations between individual flashes are minimized. The number of flashes used varies depending on the clinical chemistry. In the present embodiment, between 10 and 200 flashes are typically averaged for a given cuvette.

The present invention provides a compact, convenient, and highly automated system for the photometric analysis of fluids, typically blood or other body fluid samples from a patient. The system is capable of measuring light absorption values at a number of wavelengths. The analyzer also includes several advanced calibration and error compensation systems. As a result, the system is capable of rapidly performing a large number of chemical tests to a high degree of precision. Despite its sophistication, the analyzer is compact and inexpensive enough to allow its widespread use in hospitals, clinics, and doctors' offices. With battery power, even portable systems can be provided.

The invention has been described in some detail for purposes of clarity and illustration. Modifications to the particular embodiment described will occur to those skilled in the art. Therefore, the scope of the invention should be determined with reference to the appended claims, along with the full scope of equivalents to which those claims are entitled.

What is claimed is:

1. A method for monitoring the light intensity of a light source in a photometric fluid analyzer which lessens over time, wherein the analyzer further includes a sample rotor having a plurality of cuvettes for holding a quantity of the fluid to be analyzed and a through hole in the place of one of the cuvettes, and a light detector disposed to detect light directed through the cuvettes, the method comprising:

moving the rotor to a position wherein light from the light source is directed through the through hole;

measuring a signal from the light detector while the light is directed through the through hole and strikes the light detector at full intensity;

comparing the measured signal to a value selected to correspond to an acceptable light intensity level generated from the light source;

indicating the need to replace the light source when the measured signal differs by more than a predetermined amount from the selected value; and replacing the light source when the indicated signal differs by more than a predetermined amount from the selected value.

2. A method for compensating for the effects of scattered light in a photometric fluid analyzer having a light source, a sample rotor having a plurality of cuvettes for holding a quantity of the fluid to be analyzed and an opaque body disposed at the position of one of the cuvettes, and a light detector disposed to detect light directed through the cuvettes, the method comprising:

moving the rotor to a position wherein the opaque body disposed at the position of one of the cuvettes is aligned with the light source and the light detector so that light from the light source will be prevented from directly impinging on the light detector by the opaque body while allowing scattered light to strike the detector;

flashing the light source while the rotor is positioned to prevent the light from directly impinging on the light detector while allowing scattered light to strike the detector;

measuring a signal from the light detector while the light is prevented from directly impinging on the light detector by the rotor and while scattered light strikes the detector;

moving the rotor to a position wherein one of the cuvettes holding the fluid is aligned with the light source and the light detector so that light from the light source can be directed through the fluid and onto the light detector;

flashing the light source while the rotor is positioned to pass light through fluid in a cuvette;

measuring a signal from the light detector while the light is directed through the fluid; and modifying the signal measured when the light was directed through the fluid based on the signal measured when the scattered light struck the detector.

3. A method for determining the concentration of a substance in a fluid sample in a photometric fluid analyzer having a light source, a sample rotor having a plurality of cuvettes for holding a quantity of the fluid to be analyzed, and a light detector disposed to detect light directed through the cuvettes, the method comprising:

mixing a first quantity of the sample in an assay cuvette with a reagent selected to produce a chemical reaction between the reagent and the substance whose concentration is to be measured, the reaction producing a known reaction product;

moving the rotor to a position in which light is directed from the light source through the sample in the assay cuvette;

simultaneously measuring light transmitted through the sample in the assay cuvette at a first wavelength which is selectively absorbed by the reaction product and at a second wavelength which is not absorbed by the reaction product;

storing a first value corresponding to the amount of light transmitted through the assay cuvette at the first wavelength;

storing a second value corresponding to the amount of light transmitted through the assay cuvette at the second wavelength;

moving the rotor to a position in which light is directed through a reference cuvette not containing the reaction product;

simultaneously measuring light transmitted through the reference cuvette at the first wavelength and at the second wavelength;

storing a third value corresponding to the amount of light transmitted through the reference cuvette at the first wavelength;

storing a fourth value corresponding to the amount of light transmitted through the reference cuvette at the second wavelength;

comparing the first and second values to produce a sample value;

comparing the third and fourth values to produce a reference value; and comparing the sample and reference values to determine the concentration of the substance in the fluid sample.

* * * * *